United States Patent [19]

Shiomi et al.

[11] Patent Number: 5,248,835
[45] Date of Patent: Sep. 28, 1993

[54] METHOD OF PRODUCING A MONOALKYLETHER OF A DIHYDRIC PHENOL COMPOUND

[75] Inventors: Yasushi Shiomi; Yasuo Nakamura; Takumi Manabe; Shinichi Furusaki; Masaoki Matsuda; Muneki Saito, all of Ube, Japan

[73] Assignee: Ube Industries, Ltd., Yamaguchi, Japan

[21] Appl. No.: 868,962

[22] Filed: Apr. 16, 1992

[30] Foreign Application Priority Data

Apr. 19, 1991 [JP] Japan .................................. 3-179071
Jun. 14, 1991 [JP] Japan .................................. 3-238568

[51] Int. Cl.$^5$ ...................... C07C 41/01; C07C 41/09
[52] U.S. Cl. ................................. 568/650; 568/651; 568/652; 568/653
[58] Field of Search ............... 568/650, 652, 653, 651

[56] References Cited

U.S. PATENT DOCUMENTS

2,615,051  10/1952  Grote ................................... 568/650
4,025,566  5/1977  Nagai et al. ........................ 568/650

FOREIGN PATENT DOCUMENTS

228898  7/1987  European Pat. Off. .
420756A2  4/1991  European Pat. Off. .

OTHER PUBLICATIONS

Chemical Abstracts No. 197162, vol. 89, No. 23 (1978), corresponding to Japanese Patent Document No. JP-A-5,365,837.
Chemical Abstracts No. 120967, vol. 86, No. 17 (1977), corresponding to Japanese Patent Document No. JP-A-51,108,026.
European Search Report, EP 92 40 1073, Jul. 14, 1992.

Primary Examiner—Marianne M. Cintins
Assistant Examiner—Margaret J. Page
Attorney, Agent, or Firm—Finnegan, Henderson, Farabow, Garrett & Dunner

[57] ABSTRACT

A monoalkylether of a dihydric phenol compound is produced at a high conversion and selectivity by catalytically dehydration reacting a dihydric phenol compound with a lower monohydric alcohol in the presence of a catalyst comprising at least one inorganic substance of the empirical formula (I):

$$Al_a P_b Ti_c Si_d X_e O_f \qquad (I)$$

wherein X is an alkali metal (Group Ia) atom, alkaline earth metal (Group IIa) atom or a metal atom of Group VIII of the Periodic Table, a, b, c, d, e and f are the numbers of Al, P, Ti, Si, X and O atoms respectively, and provided that a = 1, b = 1.0 to 1.9, c = 0 05 to 0.5, d = 0.05 to 0.2, e = 0 to 0.9 and f = 4.2 to 8.1, and collecting the resultant reaction product from the reaction system.

15 Claims, No Drawings

METHOD OF PRODUCING A MONOALKYLETHER OF A DIHYDRIC PHENOL COMPOUND

BACKGROUND OF THE INVENTION

1. Field of the Invention

The present invention relates to a method of producing a monoalkylether of a dihydric phenol compound. More particularly, the present invention relates to a method of producing a monoalkylether of a dihydric phenol compound at a high conversion and selectivity by a catalytical dehydration reaction of a dihydric phenol compound with a lower monohydric alcohol in the presence of a specific dehydration reaction catalyst comprising aluminum, phosphorus, titanium, silicon, a member selected from alkali metals (Group Ia) alkaline earth metals (Group IIa) and metals of Group VIII of the Periodic table, and oxygen in a specific atomic ratio.

The specific dehydration reaction catalyst exhibits an excellent durability in a continuous dehydration reaction of the dihydric phenol compound with the lower monohydric alcohol in a gas phase over a long time, and a high mechanical strength.

The monoalkylethers of dihydric phenol compounds, for example, guaiacol and guathol, are useful as intermediate of various perfumes and medicines, or as antioxidants and stabilizers of synthetic resins.

2. Description of the Related Arts

It is known that a monoalkylether of a dihydric phenol compounds, for example, guaiacol or guathol, can be produced by a catalytic dehydration (etherification) reaction of a dihydric phenol compound with a lower monohydric alcohol in a gas phase.

In a conventional method, a monoalkylether of a dihydric phenol compound, is produced by etherifying in a liquid phase a dihydric phenol compound with an alkylating agent consisting of, for example, dimethyl sulfate, a combination of alkyl chloride with an alkali, or dimethyl carbonate. Generally, the alkylating agent usable for the liquid phase etherifying process is extremely expensive, and thus the waste liquid from the etherifying process must be clarified by a complicated process.

Various gas phase etherifying processes for producing the monoalkylethers of the dihydric phenol compounds are disclosed in the following literature:
(1) Chem. Abs., 55-7366 (1960), Masloboino-Zhirovaya Prom., 26[10], 24 to 27 (1960)
(2) West German Patent No. 827803
(3) Japanese Examined Patent Publication No. 53-35062
(4) Japanese Examined Patent Publication No. 55-33658
(5) Japanese Examined Patent Publication No. 55-6618
(6) Journal of Japan Chemical Association, [12], 23311 (1985), and Japanese Examined Patent Publication No. 56-25213

For example, an etherifying reaction of a dihydric phenol compound, for example, catechol, with a lower monohydric alcohol, for example, methyl alcohol, is carried out in a gas phase in the presence of (a) a catalyst prepared from phosphoric acid and boric acid, as disclosed in literatures (1) and (2), (b) another catalyst comprising aluminum, phosphorus, boron and oxygen, as disclosed in literatures (3), (4) and (5), or (c) still another catalyst consisting of kaolin, as disclosed in literatures (6), to produce a monoalkylether of the dihydric phenol compound, for example guaiacol.

The prior art disclosed in literatures (1) and (2), in which the catalyst (a) comprises phosphoric acid and boric acid, is disadvantageous in that the conversion to the monoalkylether is made at an unsatisfactory level of 80 to 90%, and an active catalytic component produced by the reaction of phosphoric acid with boric acid, i.e., boron phosphate ($BPO_4$), is consumed with a lapse of time, and therefore, the durability of the catalyst is not long enough for industrial use.

The prior art process disclosed in literatures (3), (4) and (5) in which the catalyst (b) comprises aluminum, boron, phosphorus, and oxygen is advantageous in that the conversion to the monoalkylether of the dihydric phenol compound is high and the duration of the $BPO_4$ is improved, but is disadvantageous in that the activity of the catalyst is reduced with a lapse of time during a long time operation, due to the consumption of $BPO_4$ and an adhesion of carbon to the catalyst surface, and the mechanical strength is also gradually lowered with a lapse of time. Therefore, the durability of the catalyst must be further improved. Further, this catalyst is disadvantageous is that, when a lowering of the activity of the catalyst occurs, the reaction temperature must be raised in line with this lowering of the catalyst activity, to maintain the conversion of the dihydric phenolic compound to the monoalkylether thereof at a desired high level, and therefore, it is very difficult to continue the etherifying reaction in a stable condition for a long time.

In the process in which the catalyst (c) consisting of kaolin is used, the conversion to the alkylether of the dihydric phenol compound is obtained at an unsatisfactory low level of about 80%, and an undesirable by-product is formed in a large amount of about 10%. Therefore, this process is not practical for industrial use.

SUMMARY OF THE INVENTION

An object of the present invention is to provide a method of producing a monoalkylether of a dihydric phenol compound in a gas phase by a dehydration (etherification) reaction of a dihydric phenol compound with a lower monohydric alcohol, at a high conversion and at a high selectivity.

Another object of the present invention is to provide a method of producing a monoalkylether of dihydric phenol compound in a gas phase from a dihydric phenol compound and a lower monohydric alcohol in the presence of a specific dehydration reaction catalyst capable of maintaining the catalytic activity thereof in a stable condition over a long time.

The above-mentioned objects can be attained by the method of the present invention for producing a monoalkylether of a dihydric phenol compound, which comprises catalytically dehydration-reacting in a gas phase a dihydric phenol compound with a lower monohydric alcohol in the presence of a dehydration reaction catalyst comprising at least one inorganic substance of the empirical formula (I):

$$Al_a\, P_b\, Ti_c\, Si_d\, X_e\, O_f \quad\quad\quad (I)$$

wherein X represents an atom selected from the group consisting of alkali metal atoms of Group Ia, alkaline earth metal atoms of Group IIa, and metal atoms of Group VIII of the Periodic Table, a, b, c, d, e, and f respectively represent the numbers of Al, P, Ti, Si, X and O atoms and the atomic ratio a:b:c:d:e:f is 1:1.0 to 1.9:0.05 to 0.5:0.05 to 0.2:0 to 0.9:4.2 to 8.1, and collecting the resultant reaction product from the reaction system.

DESCRIPTION OF THE PREFERRED EMBODIMENTS

In the method of the present invention, a dihydric phenol compound is reacted with a lower monohydric alcohol in a gas phase in the presence of a dehydration (etherification) reaction catalyst comprising at least one inorganic substance of the empirical formula (I):

$$Al_a P_b Ti_c Si_d X_e O_f \quad (I)$$

to produce a monoalkylether of the dihydric phenol compound.

In the empirical formula (I), X represents a member selected from the group consisting of alkali metal atoms of Group Ia, for example, Na, K or Li atoms, alkaline earth metal atoms of Group IIa, for example, Mg, Ca, or Sr atoms, and metal atoms of Group VIII of the Periodic Table, for example, Fe, Co, Ni, Pd and Pt, a, b, c, d, e and f respectively represent the numbers of Al, P, Ti, Si, X and O atoms and the atomic ratio a:b:c:d:e:f is 1:1.0 to 1.9:0.05 to 0.5: 0.05 to 0.2: 0 to 0.9:4.2 to 8.1.

Namely, in the inorganic substance of the empirical formula (I), the atomic ratio b/a is from 1.0/1 to 1.9/1, the atomic ratio c/a is from 0.05/1 to 0.5/1, the atomic ratio d/a is from 0.05/1 to 0.2/1, the atomic ratio e/a is 0/1 to 0.9/1, and the atomic ratio f/a is 4.2/1 to 8.1/1.

In an embodiment of the method of the present invention, the dehydration reaction catalyst comprises at least one inorganic substance of the empirical formula (II):

$$Al_{a'} P_{b'} Ti_{c'} Si_{d'} O_{f'} \quad (II)$$

wherein a', b', c', d', and f' respectively represent the numbers of Al, P, Ti, Si and O atoms and the atomic ratio b'/a' is 1.0 to 1.6, preferably 1.1 to 1.4, the atomic ratio c'/a' is 0.05 to 0.5, preferably 0.1 to 0.3, the atomic ratio d'/a' is 0.05 to 0.2, preferably 0.1 to 0.18, and the atomic ratio f'/a' is 4.2 to 6.9, preferably 4.65 to 5.95. Namely, the atomic ratio a': b':c':d':f' is 1:1.0 to 1.6:0.05 to 0.5:0.05 to 0.2:4.2:6.9, preferably 1:1.1 to 1.5:0.1 to 0.3:0.1 to 0.18:4.65 to 5.95.

In another embodiment of the method of the present invention, the dehydration reaction catalyst comprises at least one inorganic substance of the empirical formula (III):

$$Al_{a''} P_{b''} Ti_{c''} Si_{d''} X_{e''} O_{f''} \quad (III)$$

wherein X is as defined above, a", b"', c"d", e" and f" respectively represent the numbers of Al, P, Ti, Si, X and O atoms and the atomic ratio b"/a" is 1.01 to 1.9, preferably 1.15 to 1.6, the atomic ratio c"/a" is 0.05 to 0.5, preferably 0.1 to 0.3, the atomic ratio d"/a" is 0.05 to 0.2, preferably 0.1 to 0.18 the atomic ratio e"/a" is 0.01 to 0.9, preferably 0.05 to 0.6, and the atomic ratio f"/a" is 4.24 to 8.1, preferably 4.85 to 6.75.

Namely, the atomic ratio a":b":c":d":e":f" is 1:1.01 to 1.9:0.05 to 0.5:0.05 to 0.2:0.01 to 0.9:4.24 to 8.1, preferably 1:1.15 to 1.6, 0.1 to 0.3:0.1 to 0.18:0.05 to 0.6:4.85 to 6.75. Preferably in the empirical formula (III), when X is an alkali metal atom of Group Ia, the atomic ratio e"/a" is from 0.03 to 0.9, more preferably 0.15 to 0.6, when X is an alkaline earth metal atom of Group IIa, the atomic ratio a"/e" is 0.02 to 0.6, more preferably 0.1 to 0.4 and when X is a metal atom of Group VIII of the Periodic Table, the atomic ratio a"/e" is from 0.01 to 0.3, more preferably 0.05 to 0.2.

The dehydration reaction catalyst usable for the method of the present invention contains no BPO$_4$ (boron phosphate), and thus is actually free from the disadvantage that the catalytic activity of the catalyst containing BPO$_4$ is rapidly reduced within a short time due to a decrease in the content of BPO$_4$ in the catalyst.

In the dehydration reaction catalyst of the present invention, if the atomic ratio b/a is less than 1.0, i.e., the content of phosphorus is too low, the resultant catalyst exhibits an unsatisfactory catalytic activity in the dehydration reaction. Also, if the atomic ratio is more than 1.9, i.e., the content of phosphorus is too high, the resultant catalyst exhibits not only an unsatisfactory catalytic activity but also an undesirably lowered mechanical (crushing resistance) strength.

Also, if the atomic ratio c/a of the dehydration reaction catalyst of the present invention is less than 0.05, the resultant catalyst exhibits an undesirably lowered catalytic activities, and thus in the dehydration reaction of the dihydric phenol compound with the lower monohydric alcohol, the conversion of the dihydric phenol compound and the selectivity of the aimed alkylether of the dihydric phenol compound are undesirably lowered. If the atomic ratio c/a is more than 0.5, the resultant catalyst exhibits a significantly lowered catalytic activity and an unsatisfactory mechanical strength.

Further, if the atomic ratio d/a is less than 0.05, the resultant catalyst exhibits an unsatisfactory catalytic activity and a significantly lowered mechanical strength. If the atomic ratio d/a is more than 0.2, the resultant catalyst exhibits an unsatisfactory catalytic activity.

The catalyst of the present invention undesirably has strong acid points which effectively cause the starting substances of the dehydration reaction, i.e., the dihydric phenol compound and the lower monohydric alcohol, to be converted with a lapse of time to a modified substance having an undesirably raised boiling temperature and to be undesirably carbonized, and result in a significant reduction in the catalytic activity of the catalyst.

The metals of Groups Ia, IIa and VIII as represented by X in the empirical formula (I) or (III), effectively decrease the strong acid points of the dehydration reaction catalyst of the present invention.

Also, the metal X contained in the catalyst undesirably break catalytically active points of the catalyst.

Accordingly, the atomic ratio e/a must be 0.9 or less, preferably 0.01 to 0.9. If the atomic ratio e/a is more than 0.9, the resultant catalyst exhibits an unsatisfactory catalytic activity.

When the atomic ratio e/a is less than 0.01, the effect of the metal X for decreasing the strong acid points of the catalyst is sometimes unsatisfactory. If the strong acid points are contained in a very small amount in the catalyst, the catalyst need not contain the metal X.

The dehydration reaction catalyst of the present invention can be prepared in the following manner.

A starting material containing Al, P, Ti, Si and at least one metal selected from Group Ia metals, Group IIa metals and Group VIII metals, is prepared in accordance with the empirical formula (I), and then mixed with water in an amount of 0.1 to 2.0 times the dry weight of the starting material.

The mixture is the heat-treated at a temperature of from 70° C. to 110° C. for 4 to 20 hours while stirring, the heat-treated mixture is dried by a customary method, and the dried mixture is sintered in air atmosphere at a temperature of from 300° C. to 600° C.

The sintering procedure is preferably applied to the dried mixture after it has been formed into a desired shape, for example, a grain, granule or pellet, by a shaping machine, for example, a pelletizer.

The resultant sintered catalyst preferably has a form in which the catalyst can form a fixed catalyst bed or a moving catalyst bed in a reaction for the dehydration reaction. Particularly, the catalyst is preferably in the form of spherical particles, or rod or ring-shaped grains having an average size of from 0.5 to 20 mm, more preferably 1 to 10 mm. If necessary, the sintered catalyst is pulverized and screened to provide catalyst particles or grains having the above-mentioned size.

In the preparation of the dehydration catalyst of the present invention, the sintering temperature must be controlled to a level of 300° C. to 600° C. If the sintering temperature is less than 300° C. or more than 600° C., the resultant catalyst sometimes exhibits an unsatisfactory catalytic activity. There is no limitation of the sintering time, but usually the sintering time is from 1 to 10 hours.

In the preparation of the catalyst, the starting material is prepared by mixing an aluminum-containing material, a phosphorus-containing material, a titanium containing material, a silicon-containing material, and a metal X-containing material.

Aluminum-containing material preferably comprises at least one member selected from oxides of aluminum, hydroxides of aluminum, aluminum carbonate, and aluminum nitrate; which can be converted to aluminum oxide by the sintering procedure in the air atmosphere.

The phosphorus-containing material preferably comprises at least one member selected from phosphoric acids of the formula $P_2O_5 \cdot nH_2O$, for example, orthophosphoric acid, pyrophosphoric acid, metaphosphoric, tetraphosphoric acid, polymetaphosphoric acid, and unhydrated phosphoric acid.

The titanium-containing material preferably comprises at least one member selected from halides of titanium, hydroxides of titanium, oxides of titanium, and titania sol.

The silicon-containing material preferably comprises at least one member selected from halides, hydroxide, nitrogen compounds, and carbonized compounds of silicon which are capable of being converted to oxides of silicon by the sintering procedure in the air atmosphere.

The silicon compounds include silica sol and silica gel.

The metal X-containing material preferably comprises at least one member selected from oxides, hydroxides and phosphates of the metals of Group Ia, IIa and VIII. The metal X compounds are not restricted to water-soluble compounds. More preferably, the metal X-containing compound is selected from phosphates of the metals X.

The specific dehydration reaction catalyst of the present invention provides a very stable dehydration reaction. Therefore, even if the catalyst is continuously or repeatedly employed over a long time, substantially no component is eluted from the catalyst, and thus the catalytic activity of the catalyst is not substantially lowered. Nevertheless, if the catalyst is soiled by carbon or an organic substance, whereby the catalytic activity of the catalyst is lowered, the catalyst can be reactivated by sintering in the air atmosphere.

The dehydration reaction catalyst of the present invention preferably has a total pore volume of 0.3 to 0.6 ml/g and a specific surface area (BET) of 30 to 50 $m^2/g$.

In the method of the present invention, preferably a dihydric phenol compound and a lower monohydric alcohol are introduced altogether or separately from each other into an evaporator preferably having a preheating section and an evaporating section, and heat-evaporated therein. The resultant dihydric phenol compound vapor and lower monohydric alcohol vapor are fed altogether or separately from each other into a reactor, for example, a reaction tube or a reaction vessel. In this feeding step, an inert gas is optionally added to a mixture of the dihydric phenol compound vapor and the lower monohydric alcohol vapor or the each vapor.

When an inert gas is employed, the amount of the inert gas is preferably 10% or less based on the total volume of the dihydric phenol compound vapor and the lower monohydric alcohol vapor.

The reactor contains the dehydration reaction catalyst arranged therein.

In the reactor, the catalytic dehydration reaction of the dihydric phenol compound with the lower monohydric alcohol is preferably carried out at a temperature of from 200° C. to 400° C., more preferably from 230° C. to 350° C., under the ambient atmospheric pressure or a slightly pressurized condition, to produce a monoalkylether of the dihydric phenol compound.

In the method of the present invention, the dihydric phenol compound is preferably selected from the group consisting of unsubstituted dihydric phenol compounds, for example, catechol, hydroquinone and resorcinol, and substituted dihydric phenol compounds with at least one substituent selected from the group consisting of halogen atoms and lower alkyl groups preferably having 1 to 4 carbon atoms, for example, 4-methylcatechol, 2-methylcatechol, 2-methylhydroquinone, 4-chlorocatechol, 2-chlorocatechol, 2-chlorohydroquinone.

The lower monohydric alcohol usable for the present invention is preferably selected from linear and branched lower aliphatic monohydric alcohols having 1 to 6 carbon atoms, more preferably 1 to 4 carbon atoms; for example, methyl alcohol, ethyl alcohol, n-propyl alcohol, isopropyl alcohol, n-butyl alcohol, and isobutyl alcohol.

In the method of the present invention, the dihydric phenol compound is preferably fed in a feeding rate of 0.01 to 10 g/hr, more preferably 0.05 to 1.0 g/hr per $cm^3$ of the dehydration reaction catalyst into the reaction system (reactor).

Also, in the method of the present invention, the lower monohydric alcohol is preferably fed at a feeding rate of from 1 to 50 moles, more preferably 2 to 15 moles per mole of the dihydric phenol compound, into the reaction system.

In the method of the present invention, the catalytical dehydration reaction of the dihydric phenol compound with the lower monohydric alcohol in a gas phase is carried out optionally in the presence of a promoter consisting of a member selected from the group consisting of phosphorus compounds and mixtures of phosphorus compounds with boron compounds, and placed in the reaction system.

The promoter may be directly mixed with at least one of the dihydric phenol compound, the lower monohydric alcohol and a mixture thereof, the outside of the reaction system, or continuously fed into the reaction system.

In the promoter, the phosphorus compound is preferably selected from the group consisting of monoalkyl phosphates, dialkyl phosphates, and trialkyl phosphates. Also, boron phosphate can be beneficially employed as a phosphorus compound for the promoter.

The boron compound for the promoter is preferably selected from the group consisting of boric acid, monoalkyl borates, dialkyl borates, and trialkyl borates.

When the promoter is supplied into the reaction system, the promoter is preferably present in an amount of 0.01 to 2%, more preferably 0.05 to 1%, based on the total amount of the dihydric phenol compound and the lower monohydric alcohol.

When the promoter is used in a large amount of more than 2% by weight, sometimes a flow of the starting compounds and the resultant reaction product through the reaction system is blocked.

In the method of the present invention, the resultant reaction mixture is discharged from the reaction system and cooled to a temperature at which the reaction product is liquefied under the ambient atmospheric pressure. From the view point of an easy handling of the cooled reaction mixture, the cooling temperature is preferably 40° C. or less.

The liquefied reaction product is collected from the cooled reaction mixture.

The reactor usable for the method of the present invention can be selected from conventional reactors capable of being filled with the dehydration reaction catalyst, for example, ambient atmospheric pressure fixed or fluidized bed reactors through which the starting compounds and the resultant reaction product can flow in a gas phase under the ambient atmospheric pressure or a slightly raised pressure, and in which the catalyst particles or grains form a fixed bed or a fluidized bed.

In the method of the present invention, the resultant alkylether of the dihydric phenol compound, for example, guaiacol, catechol ethylester or hydroquinone monomethylether, are useful as intermediates of various perfumes and medicines and as antioxidants, and stabilizers for synthetic resins.

The method of the present invention is characterized by carrying out an etherification reaction of a dihydric phenol compound with a lower monohydric alcohol in a gas phase in the presence of a specific dehydration reaction catalyst comprising at least one inorganic material of the empirical formula (I), which comprises aluminum (Al), phosphorus (P), titanium (Ti), silicon (Si), oxygen (O) and optionally at least one metal X of Group Ia, IIa and VIII of the Periodic Table, in a specific atomic ratio.

The specific dehydration reaction catalyst of the present invention exhibits a high catalytic activity for various etherification reactions and esterification reactions. Also, the catalytic activity of the catalyst is stable and has a high durability over a long time, and an aimed product can be produced at a high conversion of the starting compound and at a high selectivity of the aimed product.

Further, after being employed for a reaction procedure, the used dehydration reaction catalyst of the present invention can be easily reactivated by a sintering procedure in the air atmosphere.

When molded into pellets or grains, the resultant grains or pellets of the catalyst exhibits a high mechanical strength, for example, crushing resistance strength, and thus can be continuously employed under a compressive force over a long time, without breaking or crushing.

Accordingly, the method of the present invention is valuable as an industrial method of producing a monoalkylether by a catalytical dehydration reaction of a dihydric phenol compound with a lower monohydric alcohol in a gas phase, at a high stability, at a high conversion of the starting compounds and at a high selectivity of the aimed compound, over a long time.

EXAMPLES

The present invention will be further illustrated by way of specific examples, which are representative and do not restrict the scope of the present invention in any way.

In the examples, the crushing resistance strength of catalyst pellets was determined in such a manner that a load was applied to a catalyst pellet in a direction of the diameter thereof, using a Kiya type hardness tester, and the load increased until the catalyst pellet was crushed. The crushing resistance strength of the catalyst pellet was represented by the crushing load. The above-mentioned measurement was repeated on 20 catalyst pellets, and the crushing resistance strength of the catalyst was represented by an average value of the measured 20 crushing loads.

EXAMPLE 1

A dispersion of 327 g of aluminum hydroxide in 877 g of water was heat-stirred at a temperature of 100° C. while refluxing, 129 g of a 26 weight % titania sol and 144 g of a 30 weight % silica sol were added to the aluminum hydroxide dispersion, and 531.6 g of a 85 weight % orthophosphoric acid were added dropwise to the dispersion at an addition rate of 12 g/minute. The resultant starting mixture was continuously stirred for 8 hours to provide a white paste.

After concentrating, the white paste was dried at a temperature of 120° C., the resultant powder was screened through a 16 mesh sieve, and the screened powder having 16 mesh size or less was molded to form rod-shaped pellets having a diameter of 6 mm and a length of 6 mm. These pellets were sintered in the air atmosphere at a temperature of 400° C. for 5 hours.

Hereinafter, the sintered pellets are referred to a dehydration reaction catalyst A.

The catalyst A had the atomic ratio of the component elements and the crushing resistance strength as shown in Table 1.

EXAMPLE 2

The same procedures as in Example 1 were carried out except that the 85 weight % orthophosphoric acid was employed in an amount of 629.5 g.

The resultant catalyst is referred to a dehydration reaction catalyst B.

The catalyst B had the atomic ratio of the component elements and the crushing resistance strength as indicated in Table 1.

EXAMPLE 3

The same procedures as in Example 1 were carried out except that the 26 weight % titania sol was used in an amount of 387.2 g.

The resultant catalyst is referred to dehydration reaction catalyst C.

The catalyst C had the atomic ratio of the component elements and the crushing resistance strength as shown in Table 1.

EXAMPLE 4

The same procedures as in Example 1 were carried out except that the starting mixture was prepared from a mixture of 327 g of aluminum hydroxide with 500 g of water, 531.6 g of a 85 weight % phosphoric acid, 129 g of a 26 weight % titania sol, and 144 g of a 30 weight % silica sol.

The resultant catalyst is referred to a dehydration reaction catalyst D.

The catalyst D had the atomic ratio of the component elements and the crushing resistance strength as shown in Table 1.

COMPARATIVE EXAMPLE 1

The same procedures as in Example 1 were carried out except that the 26 weight % titania sol was not employed.

The resultant catalyst is referred to a dehydration reaction catalyst E.

The catalyst E had the atomic ratio of the component elements and the crushing resistance strength as shown in Table 1.

COMPARATIVE EXAMPLE 2

The same procedures as in Example 1 were carried out except that the 30 weight % silica sol was not used.

The resultant catalyst is referred to a dehydration reaction catalyst F.

The catalyst F had the atomic ratio of the component elements and the crushing resistance strength as shown in Table 1.

COMPARATIVE EXAMPLE 3

The same procedures as mentioned in Example 1 were carried out except that the 85 weight % orthophosphoric acid was employed in an amount of 966.7 g.

The resultant catalyst is referred to a dehydration reaction catalyst G.

The catalyst G had the atomic ratio of the component elements and the crushing resistance strength as shown in Table 1.

COMPARATIVE EXAMPLE 4

The same procedures as in Example 1 were carried out except that the 26 weight % titania sol was employed in an amount of 1287.6 g.

The resultant catalyst is referred to a dehydration reaction catalyst H.

The catalyst H exhibited the atomic ratio of the component elements and the crushing resistance strength as shown in Table 1.

COMPARATIVE EXAMPLE 5

A starting mixture of 58.5 g of aluminum hydroxide with 46.4 g of orthoboric acid having a 14 to 42 mesh size, 172.9 g of a 85 weight % orthophosphoric acid, 19.5 g of a 30 weight % silica sol, and 160 ml of water was stirred in a flask at a temperature of 100° C. for 10 hours, to provide a white paste.

The resultant white paste was dried at a temperature of 120° C., and screened to provide catalyst particles having a 10 to 20 mesh size, and the catalyst particles were pelletized into rod-shaped pellets having a diameter of 6 mm and a length of 6 mm.

These pellets were sintered at a temperature of 400° C. in the air atmosphere for 5 hours.

The resultant catalyst is referred to a dehydration reaction catalyst I.

The catalyst I had the atomic ratio of the component elements and the crushing resistance strength as shown in Table 1.

TABLE 1

| | | Item | | | | | |
|---|---|---|---|---|---|---|---|
| | | Preparation of dehydration reaction catalyst | | | | | |
| | | Composition of starting mixture (g) | | | | | Stir-mixing |
| Example No. | | Aluminum hydroxide | Water | Titania sol (26 wt %) | Silica sol (30 wt %) | Orthophosphoric acid (85 wt %) | Temperature °C. | Time hr |
| Example | 1 | 327 g | 877 ml | 129.0 g | 144 g | 531.6 g | 100 | 8 |
| | 2 | 327 g | 877 ml | 129.0 g | 144 g | 629.5 g | 100 | 8 |
| | 3 | 327 g | 877 ml | 387.2 g | 144 g | 531.6 g | 100 | 8 |
| | 4 | 327 g | 500 ml | 129.0 g | 144 g | 531.6 g | 100 | 8 |
| Comparative Example | 1 | 327 g | 877 ml | — | 144 g | 531.6 g | 100 | 8 |
| | 2 | 327 g | 877 ml | 129.0 g | — | 531.6 g | 100 | 8 |
| | 3 | 327 g | 877 ml | 129.0 g | 144 g | 966.7 g | 100 | 8 |
| | 4 | 327 g | 877 ml | 1288 g | 144 g | 531.6 g | 100 | 8 |
| | 5 | 58.5 g | 160 ml | (*)1 (46.4 g) (H$_3$BO$_3$) | 19.5 g | 172.9 g | 100 | 10 |

| | | Item | | | | | | | |
|---|---|---|---|---|---|---|---|---|---|
| | | Preparation of dehydration reaction catalyst | | | | Resultant dehydration reaction catalyst | | | |
| | | Drying | | Sintering | | | | | Crushing resistance strength (kg) |
| Example No. | | Temperature °C. | Time hr | Temperature °C. | Time hr | Symbol of catalyst | Atomic ratio of component elements | | |
| | | | | | | | Al P Ti Si O | | |
| Example | 1 | 120 | 24 | 400 | 5 | A | 1 1.1 0.1 0.17 4.79 | | 6.30 |
| | 2 | 120 | 24 | 400 | 5 | B | 1 1.3 0.1 0.17 5.29 | | 5.98 |
| | 3 | 120 | 24 | 400 | 5 | C | 1 1.1 0.3 0.17 5.19 | | 6.40 |

TABLE 1-continued

|  |  |  |  |  |  |  |  |  |  |  |  |
|---|---|---|---|---|---|---|---|---|---|---|---|
|  | 4 | 120 | 24 | 400 | 5 | D | 1 | 1.1 | 0.1 | 0.17 | 4.79 | 6.34 |
| Comparative | 1 | 120 | 24 | 400 | 5 | E | 1 | 1.1 | 0.0 | 0.17 | 4.59 | 5.25 |
| Example | 2 | 120 | 24 | 400 | 5 | F | 1 | 1.1 | 0.1 | 0.00 | 4.45 | 3.84 |
|  | 3 | 120 | 24 | 400 | 5 | G | 1 | 2.0 | 0.1 | 0.17 | 7.04 | 3.35 |
|  | 4 | 120 | 24 | 400 | 5 | H | 1 | 1.1 | 1.0 | 0.17 | 6.59 | 4.40 |
|  | 5 | 120 | 24 | 400 | 5 | I | 1 | 2.0 | 1.0 | 0.13 | 8.26 | 5.80 |

Note: (*)1 ... In Comparative Example 5, 46.4 g of $H_3BO_3$ were used in place of titania sol.

EXAMPLE 5

A heat-resisting glass reaction tube having an inside diameter of 30 mm and a length of 400 mm was filled by the dehydration reaction catalyst A prepared in Example 1.

The catalyst stratum was heated, and when the temperature of the catalyst stratum reached 280° C., a starting compound mixture gas consisting of catecol and methyl alcohol in a molar mixing ratio of 1:3.44 and evaporated in an evaporator was fed at a feeding rate of 10.5 g/min, together with nitrogen gas, into the reaction tube for 14 hours, to thereby cause a catalytic dehydration (etherification) reaction of catecol with methyl alcohol to provide monoalkyl ester of catecol, i.e., guaiacol.

A reaction mixture gas discharged from the reaction tube was cooled to a temperature of 40° C. The resultant liquefied reaction product was collected from the cooled reaction mixture.

The reaction product was subjected to a gas chromatographic analysis, to determine the composition of the product.

A conversion of catecol in the etherification reaction and the selectivity of guaiacol in the reaction product were calculated.

Also, after the completion of the etherification reaction, the crushing resistance strength of the used dehydration reaction catalyst A pellets, and the elution in % of the catalyst A, which is a proportion weight of a portion of the catalyst A eluted and lost from the catalyst A to the original catalyst A, were determined.

The results are shown in Table 2.

COMPARATIVE EXAMPLES 6 to 9

In comparative Examples 6 to 9, the same etherification reaction procedures as in Example 5 were carried out except that the dehydration reaction catalysts E, F, G and H were respectively used in place of the catalyst A.

The conversion of the starting dihydric phenol compound, the selectivity of the aimed reaction product, the crushing resistance strength of the catalyst pellets after the completion of the reaction procedure, and the elution of the catalysts were determined.

The results are shown in Table 2.

EXAMPLE 6

The same procedures as in Example 5 were carried out except that the reaction time was changed from 14 hours to 200 hours.

The results are shown in Table 2.

EXAMPLE 7

The same procedures as in Example 5 were carried out except that the dehydration reaction catalyst A used in Example 6 for 200 hours was reactivated by resintering at 400° C. in the air atmosphere and the reactivated catalyst A was used.

The results are shown in Table 2.

COMPARATIVE EXAMPLE 10

The same procedures as in Example 5 were carried out except that the catalyst E was replaced by the dehydration reaction catalyst E prepared in Example 1.

The results are shown in Table 2.

EXAMPLES 8 and 9

In each of Examples 8 and 9, the same procedures as in Example 6 were carried out except that the starting compound mixture of catecol with methyl alcohol was added with a 0.25 weight % boron phosphate in Example 8 and with a 0.23 weight % phosphoric acid in Example 9, in the amounts as shown in Table 2.

The results are shown in Table 2.

TABLE 2

| | | | | | Item Etherification reaction conditions | | | | | |
|---|---|---|---|---|---|---|---|---|---|---|
| | | Molar contents of starting compounds | | Promoter | | Feeding rate of starting compound mixture (g/min) | Reaction | | Catalyst | |
| Example No. | | Catechol (mole) | Methyl alcohol (mole) | Type | Amount (wt %) | | Temperature (°C.) | Time (hr) | Symbol | Amount (g) |
| Example | 5 | 1.0 | 3.44 | — | — | 10.5 | 280 | 14 | A | 10.3 |
| Comparative | 6 | 1.0 | 3.44 | — | — | 10.5 | 280 | 14 | E | 10.3 |
| tive | 7 | 1.0 | 3.44 | — | — | 10.5 | 280 | 14 | F | 10.3 |
| Example | 8 | 1.0 | 3.44 | — | — | 10.5 | 280 | 14 | G | 10.3 |
| | 9 | 1.0 | 3.44 | — | — | 10.5 | 280 | 14 | H | 10.3 |
| Example | 6 | 1.0 | 3.44 | — | — | 10.5 | 280 | 200 | A | 10.3 |
| | 7 | 1.0 | 3.44 | — | — | 10.5 | 280 | 14 | A(*)2 | 10.3 |
| Comarative Example | 10 | 1.0 | 3.44 | — | — | 10.5 | 280 | 200 | E | 10.3 |
| Example | 8 | 1.0 | 3.44 | Boron phosphate | 0.25 | 10.5 | 280 | 200 | A | 10.3 |
| | 9 | 1.0 | 3.44 | Phosphoric acid | 0.23 | 10.5 | 280 | 200 | A | 10.3 |

Item

TABLE 2-continued

|  | Example No. | Result of etherification reaction | | | Crushing resistance strength of catalyst | | Elution of catalyst (wt %) |
|---|---|---|---|---|---|---|---|
|  |  | Conversion of catechol (%) | Selectivity of reaction product (%) | | Before reaction (kg) | After reaction (kg) |  |
|  |  |  | Guaiacol | Veratrol |  |  |  |
| Example | 5 | 64.7 | 98.3 | 0.7 | 6.30 | 6.31 | 0.01 |
| Comparative | 6 | 46.3 | 95.8 | 3.2 | 5.25 | 5.25 | 0.01 |
| tive | 7 | 55.7 | 97.4 | 1.0 | 3.84 | 3.81 | 0.01 |
| Example | 8 | 36.3 | 93.7 | 2.7 | 3.45 | 3.00 | 0.03 |
|  | 9 | 28.7 | 84.7 | 6.2 | 4.41 | 4.38 | 0.01 |
| Example | 6 | 63.8 | 98.5 | 0.5 | 6.30 | 6.29 | 0.01 |
|  | 7 | 64.8 | 98.3 | 0.7 | 6.29 | 6.29 | 0.01 |
| Comparative Example | 10 | 30.3 | 96.3 | 3.0 | 5.25 | 5.05 | 0.01 |
| Example | 8 | 64.7 | 98.5 | 0.5 | 6.30 | 6.30 | 0.01 |
|  | 9 | 64.7 | 98.6 | 0.4 | 6.30 | 6.30 | 0.01 |

Note: (*)2 ... The catalyst A is one used in Example 6 and thereafter reactivated by sintering.

EXAMPLES 10 and 11

The same procedures as in Example 6 were carried out except that, in Example 10, methyl alcohol was replaced by ethyl alcohol, and in Example 11, catecol was replaced by hydroquinone.

The results are shown in Table 3.

EXAMPLES 12 to 14

In Examples 12 to 14, the same procedures as in Example 5 were carried out except that the dehydration reaction catalyst A was replaced by the dehydration reaction catalysts B, C and D respectively produced in Examples 2, 3 and 4.

The results are shown in Table 3.

COMPARATIVE EXAMPLE 11

The same procedures as in Example 5 were carried out except that the dehydration reaction catalyst A was replaced by the dehydration reaction catalyst I prepared in Comparative Example 5.

The results are shown in Table 3.

EXAMPLES 15 and 16

In each of Examples 15 and 16, a heat resisting glass reaction tube having an inside diameter of 30 mm and a length of 400 mm was filled by the dehydration reaction catalyst A prepared in Example 1, and the resultant catalyst stratum was heated.

When the temperature of the catalyst stratum reached 260° C. in Example 15 and 300° C. in Example 16, a starting compound mixture consisting of catecol and methyl alcohol in a mixing molar ratio of 1:3.44 was evaporated in an evaporator, and the resultant starting compound mixture gas was fed at a feeding rate of 10.5 g/min, together with a nitrogen gas, into the reaction tube for 14 hours, to etherify catecol with methyl alcohol and to produce a dihydric phenol compound monoalkylether, namely guaiacol. The reaction mixture gas discharged from the reaction tube was cooled to a temperature of 40° C. The resultant liquefied product was collected from the reaction mixture.

The collected reaction product was subjected to a gas chromatographic analysis. The coversion of catecol and the selectivity of guaiacol in the etherification reaction were calculated. Also, the crushing resistance strength of the catalyst before and after the reaction procedure, and the elution of the catalyst in the reaction procedure, were determined.

The results are shown in Table 3.

TABLE 3

| | | Item Etherification reaction conditions | | | | | | |
|---|---|---|---|---|---|---|---|---|
| | | Typesand amounts of starting compounds | | Feeding rate of | Reaction | | Catalyst | |
| | | Dihydric phenol compound | Lower monohydric alcohol | starting compound mixture | Temperature | Time | | Amount |
| Example No. | | (mole) | (mole) | (g/min) | (°C.) | (hr) | Symbol | (g) |
| Example | 10 | 1.0 Catechol | 3.44 Ethyl alcohol | 10.5 | 280 | 200 | A | 10.3 |
|  | 11 | 1.0 Hydroquinone | 10.3 Methyl alcohol | 10.5 | 280 | 200 | A | 10.3 |
|  | 12 | 1.0 Catechol | 3.44 Methyl alcohol | 10.5 | 280 | 14 | B | 10.3 |
|  | 13 | 1.0 Catechol | 3.44 Methyl alcohol | 10.5 | 280 | 14 | C | 10.3 |
|  | 14 | 1.0 Catechol | 3.44 Methyl alcohol | 10.5 | 280 | 14 | D | 10.3 |

TABLE 3-continued

| Example No. | | | | | | | | |
|---|---|---|---|---|---|---|---|---|
| Comparative Example | 11 | 1.0 Catechol | 3.44 Methyl alcohol | 10.5 | 280 | 14 | I | 10.3 |
| Example | 15 | 1.0 Catechol | 3.44 Methyl alcohol | 10.5 | 260 | 14 | A | 10.3 |
|  | 16 | 1.0 Catechol | 10.3 Methyl alcohol | 10.5 | 300 | 14 | A | 10.3 |

| | | Item | | | | |
|---|---|---|---|---|---|---|
| | | Results of etherification reaction | | | Crushing resistance strength of catalyst | | Elution of catalyst (wt %) |
| | | Conversion of dihydric phenyl compound (%) | Selectivity of reaction product | | Before reaction (kg) | After reaction (kg) | |
| Example No. | | | Guaiacol | Veratrol | | | |
| Example | 10 | 54.2 | 97.2 (Guathol) | 1.1 (Catechol diethyl ether) | 6.30 | 6.32 | 0.01 |
| | 11 | 58.3 | 91.4 (Hydroquinone monomethyl ether) | 5.2 (Hydroquinone dimethyl ether) | 6.30 | 6.29 | 0.01 |
| | 12 | 63.2 | 98.8 | 0.6 | 5.98 | 5.96 | 0.01 |
| | 13 | 65.4 | 98.7 | 0.5 | 6.40 | 6.39 | 0.01 |
| | 14 | 64.4 | 98.6 | 0.5 | 6.34 | 6.34 | 0.01 |
| Comparative Example | 11 | 46.6 | 94.4 | 1.8 | 5.80 | 5.20 | 14.8 |
| Example | 15 | 35.3 | 100 | 0.0 | — | — | — |
| | 16 | 80.3 | 97.3 | 1.5 | — | — | — |

EXAMPLE 17

A mixture of 327 g aluminum hydroxide, 29.7 g of potassium phosphate and 877 g of water was heat-stirred at a temperature of 100° C. while refluxing, and to the mixture was added 129 g of a 26 weight % titania sol and 144 g of a 30 weight % silica sol, and thereafter, 531.6 g of a 85 weight % orthophosphoric acid were added dropwise to the mixture at an adding rate of 12 g/min. The resultant mixture was heat-stirred for 8 hours to provide a white paste.

The white paste was concentrated and then dried at a temperature of 120° C., and the dried mixture was screened through a 16 mesh sieve. The resultant mixture powder passing through the sieve was pelletized to form rod-shaped pellets having a diameter of 6 mm and a length of 6 mm. These pellets were sintered at a temperature of 400° C. in the air atmosphere for 5 hours.

The resultant catalyst is referred to a dehydration reaction catalyst A' hereinafter.

The catalyst had the atomic ratio of the component elements and the crushing resistance strength as indicated in Table 4.

EXAMPLE 18

The same procedures as in Example 17 were carried out except that potassium phosphate was employed in an amount of 14.9 g.

The resultant catalyst is referred to a dehydration reaction catalyst B'.

The atomic ratio of the component elements and the crushing resistance strength of the catalyst B' are shown in Table 4.

EXAMPLE 19

The same procedures as in Example 17 were carried out except that potassium phosphate was employed in an amount of 59.4 g.

The resultant catalyst is referred to a dehydration reaction catalyst C'.

The component element atomic ratio and the crushing resistance strength of the catalyst C' are shown in Table 4.

EXAMPLE 20

A catalyst was prepared in the same procedures as in Example 17, except that 327 g of aluminum hydroxide and 29.7 g of potassium phosphate were heat-mixed in 500 g of water at 100° C. while refluxing, and to the mixture was added 531.6 g of orthophosphoric acid, 129 g of a 26 weight % titania sol and 144 g of a 30 weight % silica sol.

The catalyst is referred to a dehydration reaction catalyst D'.

The catalyst D' had the component element atomic ratio and the crushing resistance strength as shown in Table 4.

COMPARATIVE EXAMPLE 12

The same procedures as in Example 17 were carried out except that the potassium phosphate and the 26 weight % titania sol were not employed.

The resultant catalyst is referred to a dehydration reaction catalyst E'.

The component element atomic ratio and the crushing resistance strength of the catalyst E, are shown in Table 4.

COMPARATIVE EXAMPLE 13

The same procedures as in Example 17 were carried out except that the potassium phosphate and the 30 weight % silica sol were not employed.

The resultant catalyst is referred to a dehydration reaction catalyst F'.

The catalyst F' had the component element atomic ratio and the crushing resistance strength as indicated in Table 4.

COMPARATIVE EXAMPLE 14

The same procedures as in Example 17 were carried out except that the potassium phosphate was not employed and the 85 weight % orthophosphoric acid was used in an amount of 966.7 g.

The resultant catalyst is referred to a dehydration reaction catalyst G'.

COMPARATIVE EXAMPLE 16

A mixture of 58.5 g of aluminum hydroxide, 46.4 g of orthoboric acid having a 14 to 42 mesh size, 172.9 g of a 85 weight % orthophosphoric acid, 19.5 g of a 30 weight % silica sol, and 160 ml of water was heat-agitated in a flask at 100° C. for 10 hours, to provide a white paste.

The white paste was dried and formed into particles having 10 to 20 mesh size. The particles were pelletized to form rod-shopped pellets having a diameter of 6 mm and a length of 6 mm. These pellets were sintered in the air atmosphere at 400° C. for 5 hours.

The resultant catalyst is referred to as dehydration reaction catalyst I'.

The catalyst I' exhibited the component element atomic ratio and the crushint resistance strength as shown in Table 4.

TABLE 4

| | | Item Preparation of dehydration reaction catalyst | | | | | | | | | | |
|---|---|---|---|---|---|---|---|---|---|---|---|---|
| | Composition of starting mixture | | | | | | Stir-mixing | | Drying | | Sintering | |
| Example No. | Aluminum hydroxide (g) | Water (ml) | 26 wt % titania sol (g) | 30 wt % silica sol (g) | 85 wt % orthophosphoric acid (g) | Potassium phosphate (g) | Temperature °C. | Time hr | Temperature °C. | Time hr | Temperature °C. | Time hr |
| Example 17 | 327 | 877 | 129.0 | 144 | 531.6 | 29.7 | 100 | 8 | 120 | 24 | 400 | 5 |
| 18 | 327 | 877 | 129.0 | 144 | 531.6 | 14.9 | 100 | 8 | 120 | 24 | 400 | 5 |
| 19 | 327 | 877 | 129.0 | 144 | 531.6 | 59.4 | 100 | 8 | 120 | 24 | 400 | 5 |
| 20 | 327 | 500 | 129.0 | 144 | 531.6 | 29.7 | 100 | 8 | 120 | 24 | 400 | 5 |
| Comparative Example 12 | 327 | 877 | — | 144 | 531.6 | — | 100 | 8 | 120 | 24 | 400 | 5 |
| 13 | 327 | 877 | 129.0 | — | 531.6 | — | 100 | 8 | 120 | 24 | 400 | 5 |
| 14 | 327 | 877 | 129.0 | 144 | 966.7 | — | 100 | 8 | 120 | 24 | 400 | 5 |
| 15 | 327 | 877 | 128.8 | 144 | 531.6 | — | 100 | 8 | 120 | 24 | 400 | 5 |
| 16 | 58.5 | 160 | (46.4) ($H_3BO_3$)*3 | 19.5 | 172.9 | — | 100 | 10 | 120 | 24 | 400 | 5 |

| | | Item Dehydration reaction catalyst | | | | | | |
|---|---|---|---|---|---|---|---|---|
| | Example No. | Symbol of catalyst | Al | P | Ti | Si | K | O | Crushing resistance strength (kg) |
| Example | 17 | A' | 1 | 1.13 | 0.1 | 0.17 | 0.1 | 4.92 | 6.41 |
| | 18 | B' | 1 | 1.12 | 0.1 | 0.17 | 0.05 | 4.87 | 6.20 |
| | 19 | C' | 1 | 1.17 | 0.1 | 0.17 | 0.2 | 5.07 | 6.53 |
| | 20 | D' | 1 | 1.13 | 0.1 | 0.17 | 0.1 | 4.92 | 6.44 |
| Comparative Example | 12 | E' | 1 | 1.1 | — | 0.17 | — | 4.59 | 5.25 |
| | 13 | F' | 1 | 1.1 | 0.1 | — | — | 4.45 | 3.84 |
| | 14 | G' | 1 | 2.0 | 0.1 | 0.17 | — | 7.04 | 3.45 |
| | 15 | H' | 1 | 1.1 | 1.0 | 0.17 | — | 6.59 | 4.41 |
| | 16 | I' | 1 | 2.0 | 1.0 (B)*2 | 0.13 | — | 8.26 | 5.80 |

Note: (*)3 ... In comparative Example, 46.4 g of orthoboric acid ($H_3BO_3$) were used in place of the titania sol.

The catalyst G' had the component element atomic ratio and the crushing resistance strength as shown in Table 4.

COMPARATIVE EXAMPLE 15

The same procedures as in Example 17 were carried out except that the potassium phosphate was not employed and the 26 weight % titania sol was used in an amount of 1287.6 g.

The resultant catalyst is referred to a dehydration reaction catalyst H'.

The catalyst H' had the component element atomic ratio and the crushing resistance strength as shown in Table 4.

EXAMPLE 21

A heat-resisting glass reaction tube having an inside diameter of 30 mm and a length of 400 mm was filled by the dehydration reaction catalyst A' prepared in Example 17.

The catalyst stratum was heated and when the temperature of the catalyst stratum reached 280° C., a starting compound mixture gas consisting of catechol and methyl alcohol in a molar mixing ratio of 1:3.44 and evaporated in an evaporator was fed, at a feeding rate of 10.5 g/min, together with nitrogen gas, into the reaction tube for 14 hours, to cause a catalytic dehydration (etherification) reaction of catechol with methyl alcohol and provide monoalkyl ester of catechol, i.e., guaiacol.

A reaction mixture gas discharged from the reaction tube was cooled to a temperature of 40° C. The resultant liquefied reaction product was collected from the cooled reaction mixture.

The reaction product was subjected to a gas chromatographic analysis to determine the composition of the product.

A conversion of catechol in the etherification reaction and the selectivity of guaiacol in the reaction product were calculated.

Also, after the completion of the etherification reaction, the crushing resistance strength of the used dehydration reaction catalyst A' pellets, and the elution in % of the catalyst A' which is a proportion in weight of a portion of the catalyst A eluted and lost from the catalyst A' to the original catalyst A', were determined.

The results are shown in Table 5.

COMPARATIVE EXAMPLES 17 to 20

In comparative Examples 17 to 20, the same etherification reaction procedures as in Example 21 were carried out except that the dehydration reaction catalysts E', F', G' and H' were respectively used in place of the catalyst A'.

The conversion of the starting dihydric phenol compound, the selectivity of the reaction product, the crushing resistance strength of the catalyst pellets after the completion of the reaction procedure, and the elution of the catalysts were determined.

The results are shown in Table 5.

EXAMPLE 22

The same procedures as in Example 21 were carried out except that the reaction time was changed from 14 hours to 200 hours.

The results are shown in Table 5.

EXAMPLE 23

The same procedures as in Example 21 were carried out except that the dehydration reaction catalyst A' used in Example 22 for 200 hours was reactivated by resintering at 400° C. in the air atmosphere and the reactivated catalyst A was used.

The results are shown in Table 5.

COMPARATIVE EXAMPLE 21

The same procedures as in Example 22 were carried out except that the catalyst A' was replaced by the dehydration reaction catalyst E' prepared in Example 17.

The results are shown in Table 5.

EXAMPLES 24 and 25

In each of Examples 24 and 25, the same procedures as in Example 22 were carried out except that the starting compound mixture of catechol with methyl alcohol was added with a 0.25 weight to boron phosphate in Example 24 and with a 0.23 weight % phosphoric acid in Example 25, in the amounts as shown in Table 5.

The results are shown in Table 5.

TABLE 5

| | | Amounts of starting compounds | | Promoter | | Feeding rate of starting compound mixture (g/min) | Reaction | | Catalyst | |
|---|---|---|---|---|---|---|---|---|---|---|
| Example No. | | Catechol (mole) | Methyl alcohol (mole) | Type | Amount (wt %) | | Temperature (°C.) | Time (hr) | Type (symbol) | Amount (g) |
| Example | 21 | 1.0 | 3.44 | — | — | 10.5 | 280 | 14 | A' | 10.3 |
| Comparative | 17 | 1.0 | 3.44 | — | — | 10.5 | 280 | 14 | E' | 10.3 |
| tive | 18 | 1.0 | 3.44 | — | — | 10.5 | 280 | 14 | F' | 10.3 |
| Example | 19 | 1.0 | 3.44 | — | — | 10.5 | 280 | 14 | G' | 10.3 |
| | 20 | 1.0 | 3.44 | — | — | 10.5 | 280 | 14 | H' | 10.3 |
| Example | 22 | 1.0 | 3.44 | — | — | 10.5 | 280 | 200 | A' | 10.3 |
| | 23 | 1.0 | 3.44 | — | — | 10.5 | 280 | 200 | (*)4 A' | 10.3 |
| Comparative Example | 21 | 1.0 | 3.44 | — | — | 10.5 | 280 | 200 | E' | 10.3 |
| Example | 24 | 1.0 | 3.44 | Boron phosphate | 0.25 | 10.5 | 280 | 200 | A' | 10.3 |
| | 25 | 1.0 | 3.44 | Phosphoric acid | 0.23 | 10.5 | 280 | 200 | A' | 10.3 |

| | | Results of etherification reaction | | | Catalyst | | |
|---|---|---|---|---|---|---|---|
| | | Conversion of catechol (%) | Selectivity of reaction product | | Crushing resistance strength | | Elution of catalyst (wt %) |
| Example No. | | | Guaiacol (%) | Veratrol (%) | Before reaction (kg) | After reaction (kg) | |
| Example | 21 | 63.7 | 99.1 | 0.6 | 6.41 | 6.40 | 0.01 |
| Comparative | 17 | 46.3 | 95.8 | 3.2 | 5.25 | 5.25 | 0.01 |
| tive | 18 | 55.7 | 97.4 | 1.0 | 3.84 | 3.81 | 0.01 |
| Example | 19 | 36.3 | 93.7 | 2.7 | 3.45 | 3.00 | 0.03 |
| | 20 | 28.7 | 84.7 | 6.2 | 4.41 | 4.38 | 0.01 |
| Example | 22 | 63.0 | 99.2 | 0.6 | 6.41 | 6.39 | 0.01 |
| | 23 | 62.8 | 99.5 | 0.4 | 6.41 | 6.40 | 0.01 |
| Compara- | 21 | 30.3 | 96.3 | 3.0 | 5.25 | 5.05 | 0.01 |

TABLE 5-continued

|  | | | | | | | |
|---|---|---|---|---|---|---|---|
| tive Example | | | | | | | |
| Example | 24 | 63.4 | 99.2 | 0.4 | 6.41 | 6.40 | 0.01 |
|  | 25 | 63.4 | 99.2 | 0.4 | 6.41 | 6.40 | 0.01 |

Note: (*)4 ... This catalyst was prepared by reactivating the catalyst A after used in Example 22.

EXAMPLES 26 and 27

The same procedures as in Example 22 were carried out except that in Example 26, methyl alcohol was replaced by ethyl alcohol and in Example 27, catechol was replaced by hydroquinone.

The results are indicated in Table 6.

The results are shown in Table 6.

COMPARATIVE EXAMPLE 22

The same procedures as in Example 21 were carried out except that the dehydration reaction catalyst A' was replaced by the dehydration reaction catalyst I' prepared in Comparative Example 16.

The results are shown in Table 6.

TABLE 6

| | | Item Etherification reaction conditions | | | | | |
|---|---|---|---|---|---|---|---|
| | | Amount of starting compounds | | Feeding rate of starting compound mixture (g/min) | Reaction | | Catalyst |
| | | Dihydric phenyl compound (mole) | Lower mono- hydric alcohol (mole) | | Tempera- ture (°C.) | Time (hr) | Type (Sym- bol) | Amount (g) |
| Example No. | | | | | | | | |
| Example | 26 | 1.0 Catechol | 3.44 Ethyl alcohol | 10.5 | 280 | 200 | A' | 10.3 |
|  | 27 | 1.0 Hydro- quinone | 10.3 Methyl alcohol | 10.5 | 280 | 200 | A' | 10.3 |
|  | 28 | 1.0 Catechol | 3.44 Methyl alcohol | 10.5 | 280 | 14 | B' | 10.3 |
|  | 29 | 1.0 Catechol | 3.44 Methyl alcohol | 10.5 | 280 | 14 | C' | 10.3 |
|  | 30 | 1.0 Catechol | 3.44 Methyl alcohol | 10.5 | 280 | 14 | D' | 10.3 |
| Comparative Example | 22 | 1.0 Catechol | 3.44 Methyl alcohol | 10.5 | 280 | 14 | I' | 10.3 |

| | | Item | | | | | |
|---|---|---|---|---|---|---|---|
| | | Results of etherification reaction | | | Catalyst | | |
| | | Conver- sion of dihydric phenol compound (%) | Selectivity of reaction product | | Crushing resistance strength | | Elution of catalyst (wt %) |
| | | | Guaiacol | Veratrol | Before reac- tion (kg) | After reac- tion (kg) | |
| Example No. | | | | | | | |
| Example | 26 | 40.1 | 98.6 Guathol | 0.2 | 6.41 | 6.40 | 0.01 |
|  | 27 | 43.4 | 96.6 Hydro- quinone mono- methyl- ether | 2.2 Hydro- quinone di- methyl- ether | 6.41 | 6.41 | 0.01 |
|  | 28 | 62.9 | 99.0 | 0.4 | 6.20 | 6.20 | 0.01 |
|  | 29 | 63.5 | 99.1 | 0.5 | 6.53 | 6.50 | 0.01 |
|  | 30 | 64.2 | 99.0 | 0.4 | 6.44 | 6.42 | 0.01 |
| Comparative Example | 22 | 46.6 | 94.4 | 1.8 | 5.80 | 5.20 | 14.8 |

EXAMPLES 28 to 30

In Examples 28 to 30, the same procedures as in Examples 21 were carried out except that the dehydration reaction catalyst A' was replaced by the dehydration reaction catalysts B', C' and D' respectively produced in Examples 18, 19 and 20.

Example 31

A mixture of 327 g of aluminum hydroxide and 65 g of calcium phosphate with 877 g of water was heat-stirred at 100° C. while refluxing, and to the mixture was added 129 g of a 26 weight % titania sol and 144 g of a 30 weight % silica sol, and then 531.6 g of a 85 weight % orthophosphoric acid were added dropwise to the mixture at an adding rate of 12 g/min. The resultant mixture was continuously heat-stirred for 8 hours to provide a white paste.

After concentrating, the white paste was dried at 120° C. and the resultant powder was screened through a 16 mesh sieve. The screened powder was pelletized to form pellets having a diameter of 6 mm and a length of 6 mm, and the pellets were sintered at 400° C. in the air atmosphere for 5 hours.

The resultant catalyst is referred to as dehydration reaction catalyst J.

The catalyst J had the component element atomic ratio and the crushing resistance strength as shown in Table 7.

EXAMPLE 32

The same procedures as in Example 31 were carried out except that the calcium phosphate was used in an amount of 130 g.

The resultant catalyst is referred to as dehydration reaction catalyst K.

The catalyst K had the component element atomic ratio and the crushing resistance strength as shown in Table 7.

EXAMPLE 33

The same procedures as in Example 31 were carried out except that the calcium phosphate was used in an amount of 260 g.

The resultant catalyst is referred to as dehydration reaction catalyst L. The catalyst L had the component element atomic ratio and the crushing strength as shown in Table 7.

EXAMPLE 34

The same procedures as in Example 31 were carried out except that the calcium phosphate was replaced by 132 g of barium phosphate.

The resultant catalyst is referred to a dehydration reaction catalyst M.

The catalyst M had the component element atomic ratio and the crushing strength as indicated in Table 7.

EXAMPLE 35

The same procedures as in Example 31 were carried out except that the calcium phosphate was replaced by 66 g of cobalt phosphate.

The resultant catalyst is referred to as dehydration reaction catalyst N.

The catalyst N had the component element atomic ratio and the crushing resistance strength as shown in Table 7.

EXAMPLE 36

The same procedures as in Example 35 were carried out except that the cobalt phosphate was replaced by 93.6 g of iron phosphate.

The resultant catalyst is referred to as dehydration reaction catalyst O.

This catalyst had the component element atomic ratio and the crushing resistance strength as shown in Table 7.

TABLE 7

| | Preparation of dehydration reaction catalyst (*)5 Amounts of component compounds | | | | | | Catalyst | | | | | | |
|---|---|---|---|---|---|---|---|---|---|---|---|---|---|
| Example No. | Aluminum hydroxide (g) | Water (ml) | 26 wt % titania sol (g) | 30 wt % silica sol (g) | 85 wt % orthio-phosphoric acid (g) | Type and amount of metal X (g) | Symbol | Al | P | Ti | Si | Metal X | O | Crushing resistance strength (kg) |
| Example 31 | 327 | 877 | 129.0 | 144 | 531.6 | Calcium phosphate 65 | J | 1 | 1.18 | 0.1 | 0.17 | Ca 0.08 | 5.11 | 6.01 |
| 32 | 327 | 877 | 129.0 | 144 | 531.6 | Calcium phosphate 130 | K | 1 | 1.27 | 0.1 | 0.17 | Ca 0.17 | 5.47 | 6.35 |
| 33 | 327 | 877 | 129.0 | 144 | 531.6 | Calcium phosphate 260 | L | 1 | 1.43 | 0.1 | 0.17 | Ca 0.33 | 6.11 | 6.00 |
| 34 | 327 | 877 | 129.0 | 144 | 531.6 | Barium phosphate 132 | M | 1 | 1.23 | 0.1 | 0.17 | Ba 0.13 | 5.31 | 5.37 |
| 35 | 327 | 877 | 129.0 | 144 | 531.6 | Cobalt phosphate 66 | N | 1 | 1.19 | 0.1 | 0.17 | Co 0.09 | 5.15 | 5.92 |
| 36 | 327 | 877 | 129.0 | 144 | 531.6 | Iron phosphate 93.6 | O | 1 | 1.20 | 0.1 | 0.17 | Fe 0.10 | 5.19 | 6.28 |

Note: (*)5
Str-mixing: 100° C., 8 hours
Drying: 120° C., 24 hours
Sintering: 400° C., 5 hours

EXAMPLE 37 to 42

In Examples 37 to 42, a heat resisting glass reaction tube having an inside diameter of 30 mm and a length of 400 mm was filled by the dehydration reaction catalysts J to O respectively prepared in Example 31 to 36, and the resultant catalyst stratum was heated.

When the temperature of the catalyst stratum reached 280° C., a starting compound mixture consisting of catechol and methyl alcohol in a molar mixing ratio of 1:3.44 was evaporated in a evaporator, and the resultant starting compound mixture gas was fed in a feeding rate of 10.5 g/min. together with a nitrogen gas into the reaction tube for 14 hours, to etherify catechol with methyl alcohol and to produce a dihydric phenol compound monoalkylether, i.e., guaiacol. The reaction mixture gas discharged from the reaction tube was cooled to a temperature of 40° C. The resultant liquefied product was collected from the reaction mixture.

The collected reaction product was subjected to a gas chromatographic analysis. The conversion of catechol and the selectivity of guaiacol in the etherification reaction were calculated. Also, the crushing resistance strength of the catalyst before and after the reaction procedure, and the elution of the catalyst in the reaction procedure, were determined.

The results are shown in Table 8.

TABLE 8

| | | Etherification reaction conditions | | | | | | Results of etherification reaction | | | Catalyst | | |
|---|---|---|---|---|---|---|---|---|---|---|---|---|---|
| | | Amounts of starting compounds | | Feeding rate of starting compound mixture (g/min) | Reaction | | Catalyst | | Conversion of catechol (%) | Selectivity of reaction product | | Crushing resistance strength | | Elution of catalyst (wt %) |
| Example No. | | Catechol (mole) | Methyl alcohol (mole) | | Temperatue (°C.) | Time (hr) | Symbol | Amount (g) | | Guaiacol (%) | Veratrol (%) | Before reaction (kg) | After reaction (kg) | |
| Ex- | 37 | 1.0 | 3.44 | 10.5 | 280 | 14 | J | 10.3 | 77.6 | 98.1 | 1.2 | 6.01 | 6.00 | <0.01 |
| am- | 38 | 1.0 | 3.44 | 10.5 | 280 | 14 | K | 10.3 | 79.1 | 97.9 | 1.3 | 6.35 | 6.34 | <0.01 |
| ple | 39 | 1.0 | 3.44 | 10.5 | 280 | 14 | L | 10.3 | 80.1 | 97.9 | 1.1 | 6.00 | 5.99 | <0.01 |
| | 40 | 1.0 | 3.44 | 10.5 | 280 | 14 | M | 10.3 | 64.6 | 98.4 | 1.1 | 5.37 | 5.36 | <0.01 |
| | 41 | 1.0 | 3.44 | 10.5 | 280 | 14 | N | 10.3 | 72.3 | 97.7 | 1.7 | 5.92 | 5.91 | <0.01 |
| | 42 | 1.0 | 3.44 | 10.5 | 280 | 14 | O | 10.3 | 60.3 | 99.4 | 0.4 | 6.28 | 6.27 | <0.01 |

EXAMPLES 43 to 44

In each of Examples 43 and 44, a heat resisting glass reaction tube having an inside diameter of 30 mm and a length of 400 mm was filled by the dehydration reaction catalyst A' prepared in Example 17, and the resultant catalyst stratum was heated.

When the temperature of the catalyst stratum reached 260° C. in Example 43 and 300° C. in Example 44, a starting compound mixture consisting of catechol and methyl alcohol in a mixing molar ratio of 1:3.44 was evaporated in an evaporator, and the resultant starting compound mixture gas was fed in a feeding rate of 10.5 g/min. together with a nitrogen gas into the reaction tube for 14 hours, to etherify catechol with methyl alcohol and to produce a dihydric phenol compound monoalkylether, i.e., guaiacol. The reaction mixture gas discharged from the reaction tube was cooled to a temperature of 40° C. The resultant liquefied product was collected from the reaction mixture.

The collected reaction product was subjected to a gas chromatographic analysis. The conversion of catechol and the selectivity of guaiacol in the etherification reaction were calculated. The results are shown in Table 9.

presence of a dehydration reaction catalyst comprising at least one inorganic substance of the empirical formula (I):

$$Al_a P_b Ti_c Si_d X_e O_f \quad (I)$$

wherein X represents an atom selected from the group consisting of alkali metal atoms of group Ia, alkaline earth metal atoms of group IIa, and metal atoms of group VIII of the Periodic Table, and wherein a, b, c, d, e and f respectively represent the numbers of Al, P, Ti, Si, X and O atoms, and the atomic ratio a:b:c: d:e:f is 1:1.0 to 1.9:0.05 to 0.5:0.05 to 0.2:0 to 0.9:4.2 to 8.1, wherein said dehydration reaction catalyst contains no BPO4; and collecting the resultant reaction product from the reacting system.

2. The method as claimed in claim 1, wherein the dehydration reaction catalyst comprises at least one inorganic substance of the emperical formula (II):

$$Al_{a'} P_{b'} Ti_{c'} Si_{d'} O_{f'} \quad (II)$$

wherein a', b', c', d' and f' are the numbers of Al, P, Ti, Si and O atoms respectively and the atomic ratio a':b':c':d':f' is 1:1.0 to 1.6:0.05 to 0.5:0.05 to 0.2:4.2 to 6.9.

3. The method as claimed in claim 1, wherein the dehydration reaction catalyst comprises at least one inorganic substance of the empirical formula (III):

$$Al_{a''} P_{b''} Ti_{c''} Si_{d''} X_{e''} O_{f''} \quad (III)$$

wherein X is as defined in claim 1, a'', b'', c'', d'', e'' and f'' are the numbers of Al, P, Ti, Si, X and O atoms, respectively, and the atomic ration a'':b'':c'':d'':e'':f'' is 1:1.01 to 1.9:0.05 to 0.5:0.05 to 0.2:0.01 to 0.9:4.24 to 8.1.

TABLE 9

| | Etherification reaction conditions | | | | | | | Results of etherification reaction | | |
|---|---|---|---|---|---|---|---|---|---|---|
| | Amounts of starting compounds | | Feeding rate of starting compound mixture (g/min) | Reaction | | Catalyst | | Conversion of catechol (%) | Selectivity of reaction product | |
| Example No. | Catechol (mole) | Methyl alcohol (mole) | | Temperature (°C.) | Time (hr) | Symbol | Amount (g) | | Guaiacol | Veratrol |
| Example 43 | 1.0 | 3.44 | 10.5 | 260 | 14 | A' | 10.3 | 37.9 | 100 | —0 |
| 44 | 1.0 | 10.3 | 10.5 | 300 | 14 | A' | 10.3 | 83.2 | 97.1 | 1.7 |

We claim:

1. A method of producing a monoalkylether of a dihydric phenol compound, comprising catalytically dehydration-reacting in a gas phase a dihydric phenol compound with a lower monohydric alcohol in the 4. The method as claimed in claim 3, wherein the empirical formula (III) $Al_{a''}$, $P_{b''}$, $Ti_{c''}$, $Si_{d''}$, $X_{e''}$, and $O_{f''}$, when X is an alkali metal atom of Group Ia, the atomic ratio e"/a" if from 0.03 to 0.9, when X is an alkaline earth metal atom of Group IIa, the atomic ratio e"/a" is 0.02 to 0.6, and X is a metal atom of Group VIII of the Periodic Table, the atomic ratio e"/a" is from 0.01 to 0.3.

5. The method as claimed in claim 1, wherein the dehydration reaction catalyst is a sintering product produced in such a manner that a starting material containing Al, P, Ti, Si and at least one element represent by X in the empirical formula (I) is mixed with water in an amount of 0.1 to 2.0 times the dry weight of the starting material, the mixture is heat-treated at a temperature of from 70° C. to 110° C. while stirring, and the resultant heat treated material is dried and sintered in the air atmosphere at a temperature of from 300° C. to 600° C.

6. The method as claimed in claim 1, wherein the dehydration reaction catalyst has a total pore volume of 0.3 to 0.6 ml/g and a specific surface area BET of 30 to 50 $m^2/g$.

7. The method as claimed in claim 1, wherein the catalytical dehydration reaction is carried out at a temperature of from 200° C. to 400° C.

8. The method as claimed in claim 1, wherein the dihydric phenol compound is selected from the group consisting of catechol, hydroquinone and resorcinol compounds which are unsubstituted or substituted with at least one substituent selected from the group consisting of halogen atoms and alkyl groups having 1 to 4 carbon atoms.

9. The method as claimed in claim 1, wherein the lower monohydric alcohol is selected from aliphatic monohydric alcohols having 1 to 6 carbon atoms.

10. The method as claimed in claim 1, wherein the dihydric phenol compound is fed at a feeding rate of from 0.01 to 10 g/hr per g of the dehydration reaction catalyst into the reaction system.

11. The method as claimed in claim 1, wherein the lower monohydric alcohol is fed at a feeding rate of from 1 to 50 moles per mole of the dihydric phenol compound into the reaction system.

12. The method as claimed in claim 1, wherein the catalytical dehydration reaction of the dihydric phenol compound with the lower monohydric alcohol is carried out in the presence of a promoter selected form the group consisting of phosphorous compounds and mixtures of phosphorus compounds with boron compounds.

13. The method as claimed in claim 12, wherein the phosphorus compound is selected form the group consisting of monoalkyl phosphates, dialkyl phosphates and trialkyl phosphate and boron phosphate.

14. The method as claimed in claim 12, wherein the boron compound is selected from the group consisting of boric acid, monoalkyl borates, dialkyl borates and trialkyl borates.

15. The method as claimed in claim 12, wherein the promoter is fed at an amount of 0.01 and 2% based on the total weight of the dihydric phenol compound and the lower monohydric alcohol in the reaction system.

* * * * *

UNITED STATES PATENT AND TRADEMARK OFFICE
CERTIFICATE OF CORRECTION

PATENT NO. : 5,248,835
DATED : September 28, 1993
INVENTOR(S) : Yasushi Shiomi et al.

It is certified that error appears in the above-identified patent and that said Letters Patent is hereby corrected as shown below:

In the Abstract, beneath line 7 (formula (I)), delete ":"; and line 12, delete "0 05" and insert --0.05--.

Claim 1, column 26, line 28, delete "a:b:c:　d:e:f" and insert --a:b:c:d:e:f --.

Claim 2, column 26, line 37 (in formula (II)), delete "$O_f$," and insert --$O_f'$--.

Claim 3, column 26, line 46 (in formula (III)), delete "$O_f$," and insert --$O_f''$--; and line 50, delete "ration" and insert --ratio--.

Claim 4, column 26, line 66, after "wherein" insert --in--; line 68, delete "$O_f'$" and insert --$O_f''$--.

Claim 4, column 27, line 1, delete "if" and insert --is--.

UNITED STATES PATENT AND TRADEMARK OFFICE
CERTIFICATE OF CORRECTION

PATENT NO. : 5,248,835
DATED : September 28, 1993
INVENTOR(S) : Yasushi Shiomi et al It is certified that error appears in the above-indentified patent and that said Letters Patent is hereby corrected as shown below:

Claim 5, column 27, line 9, delete "represent" and insert --represented--.

Signed and Sealed this

Fifth Day of April, 1994

BRUCE LEHMAN

*Attest:*

*Attesting Officer*     *Commissioner of Patents and Trademarks*